(12) United States Patent
Leibowitch

(10) Patent No.: US 9,198,912 B2
(45) Date of Patent: Dec. 1, 2015

(54) SCHEDULES FOR ADMINISTERING COMBINATION THERAPIES USEFUL FOR TREATING PERSONS AFFLICTED WITH THE HUMAN IMMUNODEFICIENCY VIRUS (HIV)

(75) Inventor: Jacques Leibowitch, Paris (FR)

(73) Assignees: L'ASSISTANCE PUBLIQUE—HOPITAUX DE PARIS, Paris (FR); THE UNIVERSITY OF VERSAILLES SAINT-QUENTIN-EN-YVELINES, Versailles Cedex (FR)

( * ) Notice: Subject to any disclaimer, the term of this patent is extended or adjusted under 35 U.S.C. 154(b) by 0 days.

(21) Appl. No.: 13/511,011

(22) PCT Filed: Nov. 19, 2010

(86) PCT No.: PCT/EP2010/067851
§ 371 (c)(1),
(2), (4) Date: Jun. 19, 2012

(87) PCT Pub. No.: WO2011/061302
PCT Pub. Date: May 26, 2011

(65) Prior Publication Data
US 2012/0283177 A1    Nov. 8, 2012

(30) Foreign Application Priority Data
Nov. 20, 2009    (EP) ..................................... 09176666

(51) Int. Cl.
| | | |
|---|---|---|
| A61K 31/675 | (2006.01) | |
| A61K 31/52 | (2006.01) | |
| A61P 31/18 | (2006.01) | |
| A61K 38/07 | (2006.01) | |
| A61K 31/635 | (2006.01) | |
| A61K 31/538 | (2006.01) | |
| A61K 31/708 | (2006.01) | |
| A61K 31/665 | (2006.01) | |
| A61K 31/536 | (2006.01) | |
| A61K 31/34 | (2006.01) | |
| A61K 31/426 | (2006.01) | |
| A61K 31/4418 | (2006.01) | |
| A61K 31/505 | (2006.01) | |
| A61K 31/513 | (2006.01) | |
| A61K 31/661 | (2006.01) | |
| A61K 31/7068 | (2006.01) | |

(52) U.S. Cl.
CPC .............. *A61K 31/536* (2013.01); *A61K 31/34* (2013.01); *A61K 31/426* (2013.01); *A61K 31/4418* (2013.01); *A61K 31/505* (2013.01); *A61K 31/513* (2013.01); *A61K 31/52* (2013.01); *A61K 31/661* (2013.01); *A61K 31/675* (2013.01); *A61K 31/7068* (2013.01)

(58) Field of Classification Search
None
See application file for complete search history.

(56) References Cited

U.S. PATENT DOCUMENTS

2012/0270828 A1    10/2012    Leibowitch

OTHER PUBLICATIONS

Physicians' Desk Reference. Atripla. National Drug Code: 35356-064-30.*
Cohen et al. Hiv Clin Trials 2007;8(1):19-23.*
Dybul et al. PNAS. 2001;98(26):15161-15166.*
Cohen et al., "Pilot Study of a Novel Short-Cycle Antiretroviral Treatment Interruption Strategy: 48-Week Results of the Five-Days-On, Two-Days-Off (FOTO) Study", 8(1):19-23 (2007).
Ananworanich, et al. "Failures of 1 week on, 1 week off antiretroviral therapies in a randomized trial." AIDS, 2003, 17: F33-F37.
Martin, et al. "Relationship between Adherence Level, Type of the Antiretroviral Regimen, and Plasma HIV Type 1 RNA Viral Load: A Prospective Cohort Study." AIDS Research and Human Retroviruses, 2008, vol. 24, No. 10, pp. 1263-1268.
Parienti, et al. "Not All Missed Doses Are the Same: Sustained NNRTI Treatment Interruptions Predict HIV Rebound at Low-to-Moderate Adherence Levels." PLoS ONE, Jul. 2008, vol. 3, Issue 7, e2783.
Rudy et al. "Short-Cycle Therapy in Adolescents after Continuous Therapy with Established Viral Suppression: The Impact on Viral Load Suppression." AIDS Research and Human Retroviruses, vol. 25: No. 6, 2009; p. 555-561.
Parienti et al. "Not All Missed Doses Are the Same: Sustained NNRTI Treatment Interruptions Predict HIV Rebound at Low-to-Moderate Adherence Levels." PLoS ONE, vol. 3: No. 7, 2008; e2783.
Hammer S.M.et al., "Treatment for adult HIV infection: 2006 recommendations of the International AIDS Society-USA panel.", JAMA, vol. 296, N° 7, Aug. 2006, pp. 827-843.
Gazzard B. et al.,"British HIV Association (BHIVA) guidelines for the treatment of HIV-infected adults with antiretroviral therapy", HIV Med, vol. 7, N° 8, Nov. 2006, pp. 487-503.

(Continued)

*Primary Examiner* — Amber D Steele
*Assistant Examiner* — Schuyler Milton
(74) *Attorney, Agent, or Firm* — Porzio, Bromberg & Newman, P.C.

(57) ABSTRACT

The invention relates to a pharmaceutical composition for treating the human immunodeficiency virus (HIV) in humans, including three or four active principles selected as: a nucleoside reverse transcriptase inhibitor (NARTI) selected from lamivudine and emtricitabine; a nucleoside or nucleotide reverse transcriptase inhibitor (NARTI) selected from didanosine, abacavir and tenofovir; and the combination of ritonavir with a protease inhibitor (PI) selected from lopinavir, fosamprenavir, atazanavir and darunavir; or an non-nucleoside reverse transcriptase inhibitor (NNRTI) selected from efavirenz and etravirine; for daily administration to said human being one to four days per week.

8 Claims, 15 Drawing Sheets

(56) References Cited

OTHER PUBLICATIONS

Domingo P. et al., "First line natiretroviral therapy with efavirenz or lopinavir/ritonavir plus two nucleoside analogues: the SUSKA study, a non-randomized comparison from the Vach cohort", Journal of Antimicrob.Chemother., vol. 61, N° 6, Jun. 2008, pp. 1348-1358.

Lapadula G. et al, "Risk of early virological Failure of once-daily tenofovir-emtricitabine plus twice-daily nevirapine in antiretroviral therapy-naive HIV-infected patients", Clin. Infect. Dis., vol. 46, N° 7, Apr. 2008, pp. 1127-1129.

Rey D. et al, " High rate of early virological failure with the once-daily tenofovir/mlamivudine/nevirapine combination in naive HIV-1-onfected patients-authors' repsonse", J. Antimicrob. Chemother, vol. 63, N° 5, Feb. 2009, pp. 1080-1081.

Pinheiro et al., "A survey of the syntheses of active pharmaceutical ingredients for antiretroviral drug combinations critical to access in emerging nations.", Antiviral Research, vol. 79, N° 3, Sep. 2008, pp. 143-165.

Project inform, Standard dosing Chart for anti-HIV drugs, Jan. 2006.

Leon A et al, "Early virological failure in treatment-naive HIV-infected adults receiving didanosine and tenofovir plus efavirenz or neviraine", AIDS, vol. 19, N° 2, Jan. 2005, pp. 213-215.

Arribas J.R., "The rise and fall of triple nucleoside reverse transcriptase inhibitor regimens", J. Antimicrob. Chemother, vol. 54, Jul. 2004, pp. 587-592.

International Search Report dated Feb. 8, 2011, from the corresponding patent application.

International Search Report dated Feb. 8, 2011, from the patent application WO2011/061303.

\* cited by examiner

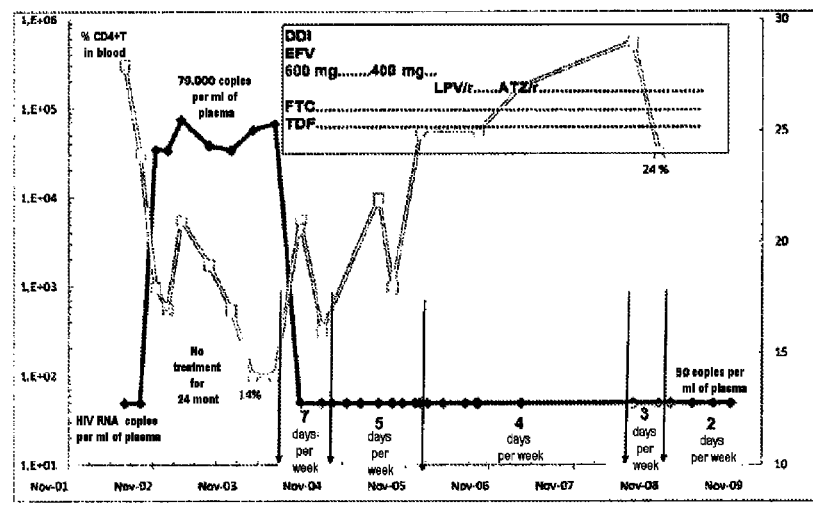
Fig.1 (Example 1)
FTC: emtricitabine; DDI: didanosine; TDF: tenofovir; EFV: efavirenz; r: ritonavir; LPV: lopinavir; ATZ: atazanavir.

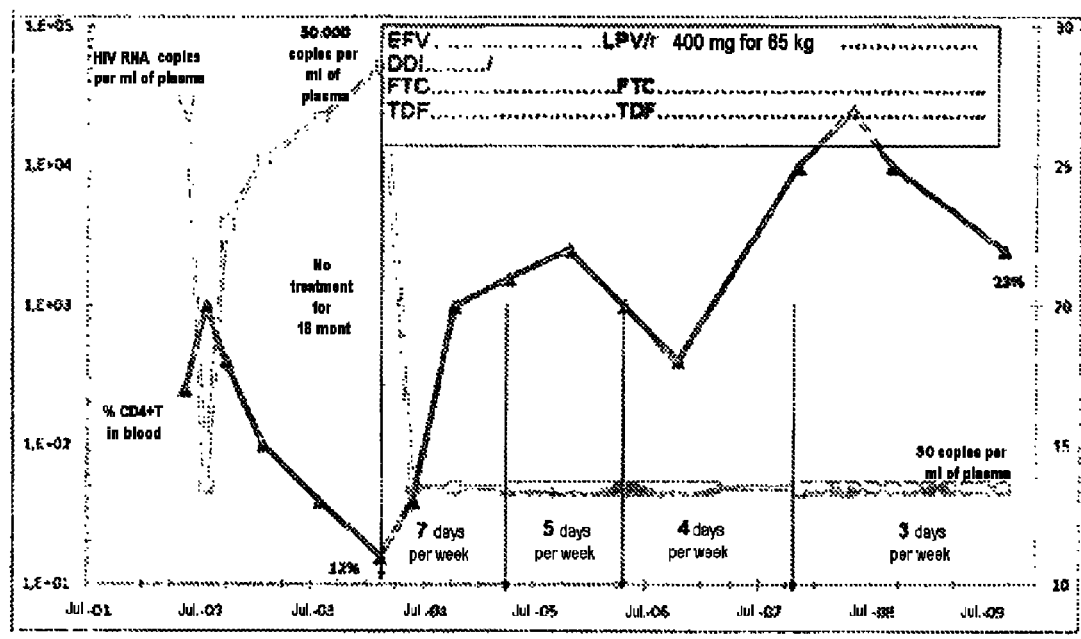
Fig.2 (Example2)
FTC : emtricitabine ; DDI : didanosine ; TDF : tenofovir ; EFV : efavirenz ; r : ritonavir ; LPV : lopinavir.

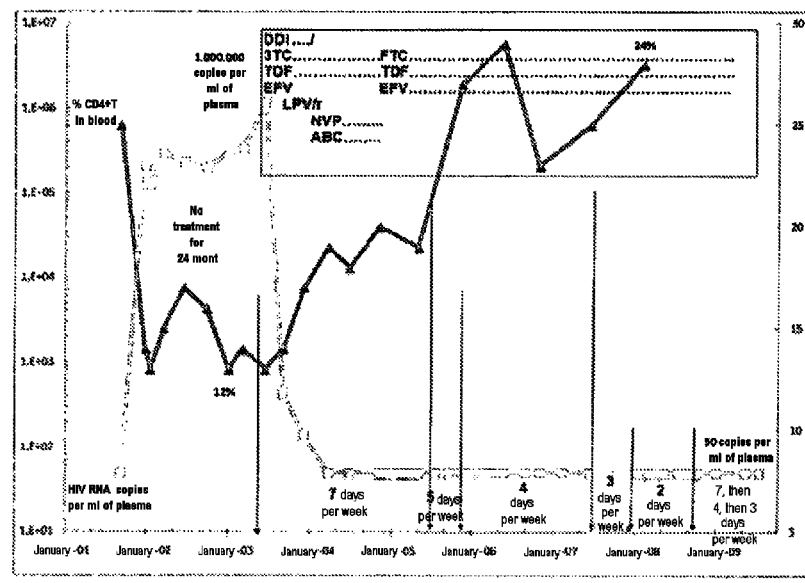
Fig.3 (Example3)
3TC : lamivudine ; FTC : emtricitabine ; DDI : didanosine ; ABC : abacavir ; TDF tenofovir ; NVP : nevirapine ; EFV : efavirenz ; r : ritonavir ; LPV : lopinavir.

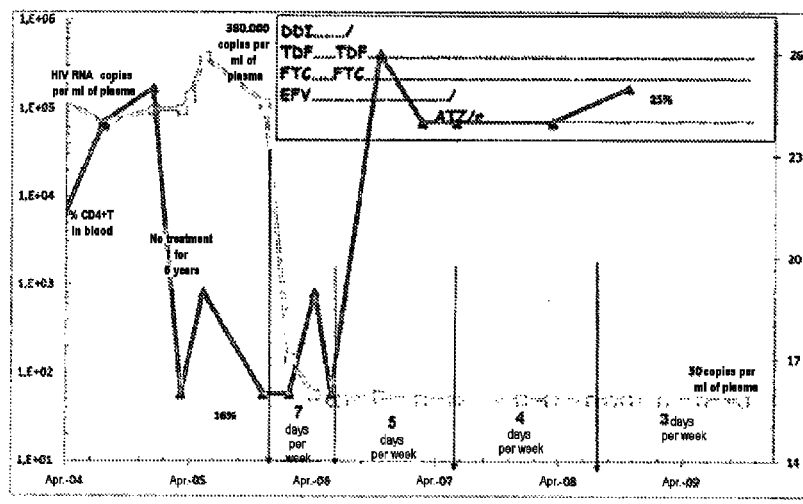
Fig.4 (Example 4)
FTC : emtricitabine ; DDI : didanosine ; TDF : tenofovir ; EFV : efavirenz ; r : ritonavir ; ATZ : atazanavir.

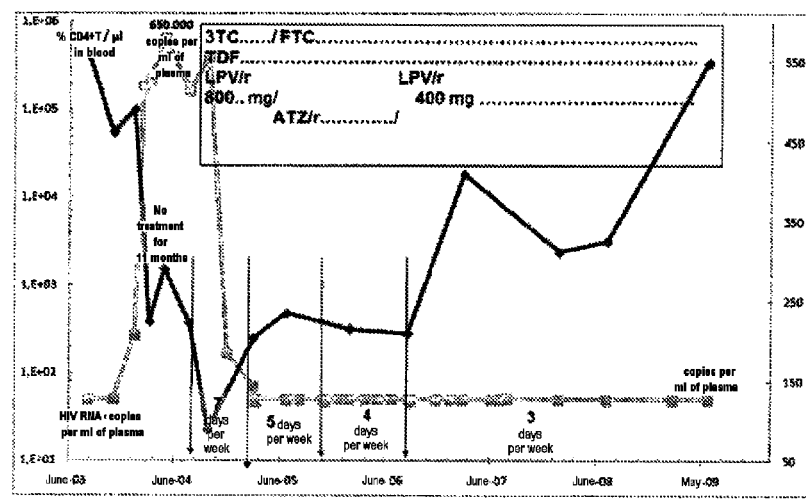
Fig.5 (Example 5)
3TC: lamivudine; FTC: emtricitabine; TDF: tenofovir; r: ritonavir; LPV: lopinavir; ATZ: atazanavir.

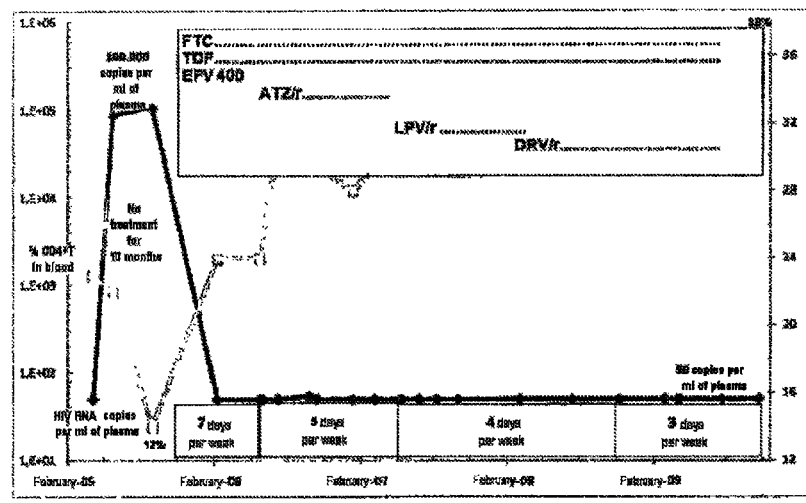
Fig.6 (Example 6)
FTC : emtricitabine ; TDF : tenofovir ; EFV : efavirenz ; r : ritonavir ; LPV : lopinavir ; ATZ : atazanavir ; DRV : darunavir.

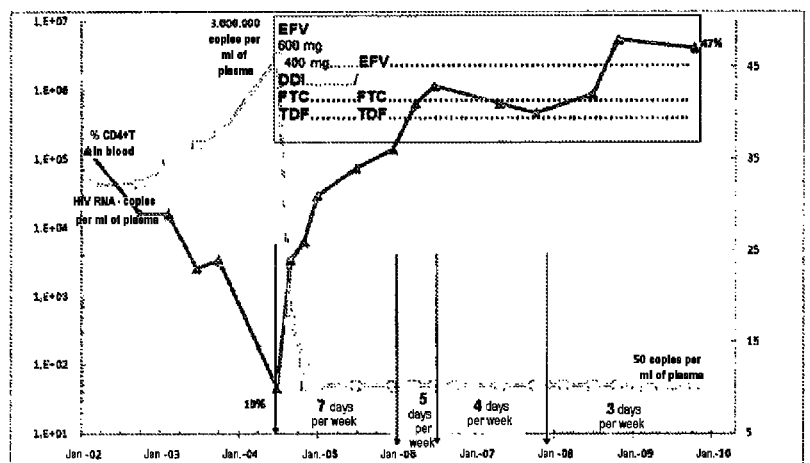
Fig.7 (Example 7)
FTC : emtricitabine ; DDI : didanosine ; TDF : tenofovir ; EFV : efavirenz.

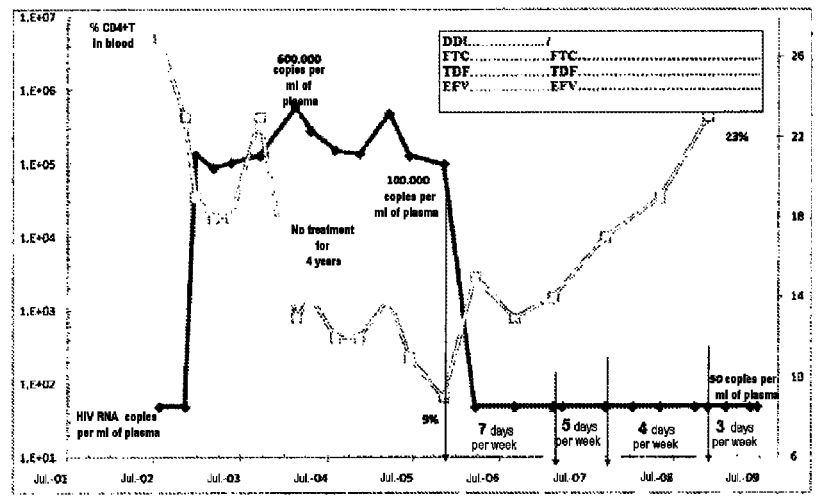
Fig.8 (Example 8)
FTC : emtricitabine ; DDI : didanosine ; TDF : tenofovir ; EFV : efavirenz.

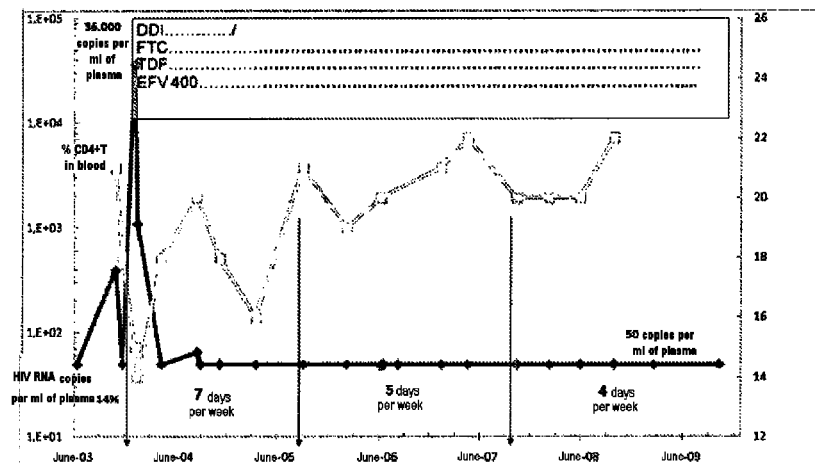
Fig.9 (Example9)
FTC : emtricitabine ; DDI : didanosine ; TDF : tenofovir ; EFV : efavirenz.

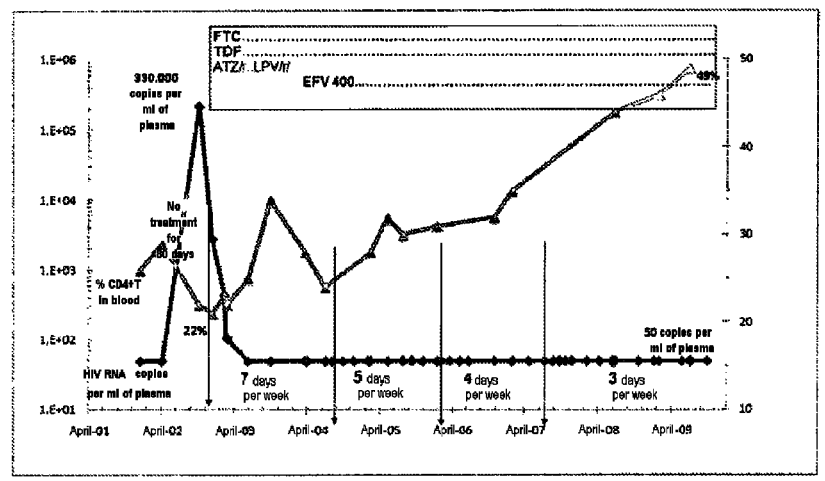
Fig.10 (Example 10)
FTC : emtricitabine ; TDF : tenofovir ; EFV : efavirenz ; r : ritonavir ; LPV lopinavir ; ATZ atazanavir.

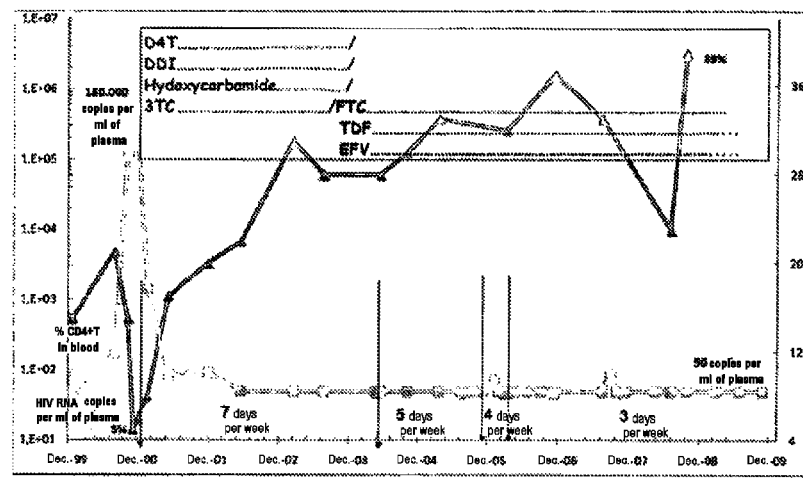
Fig.11 (Example 11)
FTC : emtricitabine ; TDF : tenofovir ; EFV : efavirenz.

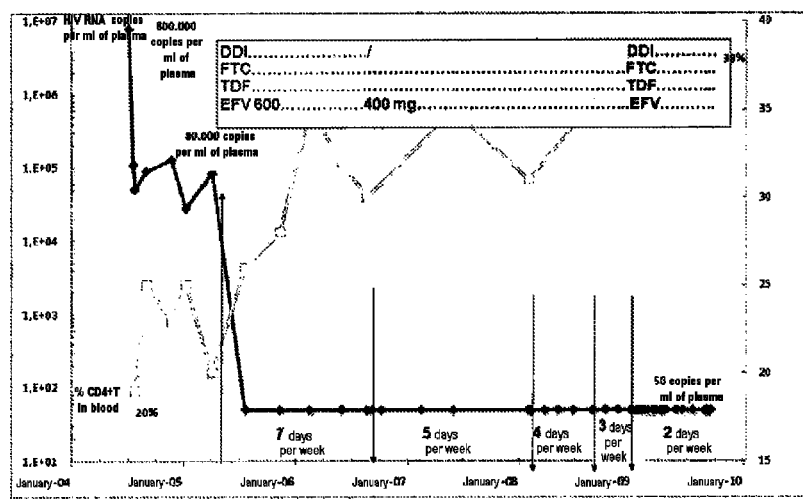
Fig.12 (Example 12)
FTC : emtricitabine ; DDI : didanosine ; TDF : tenofovir ; EFV : efavirenz.

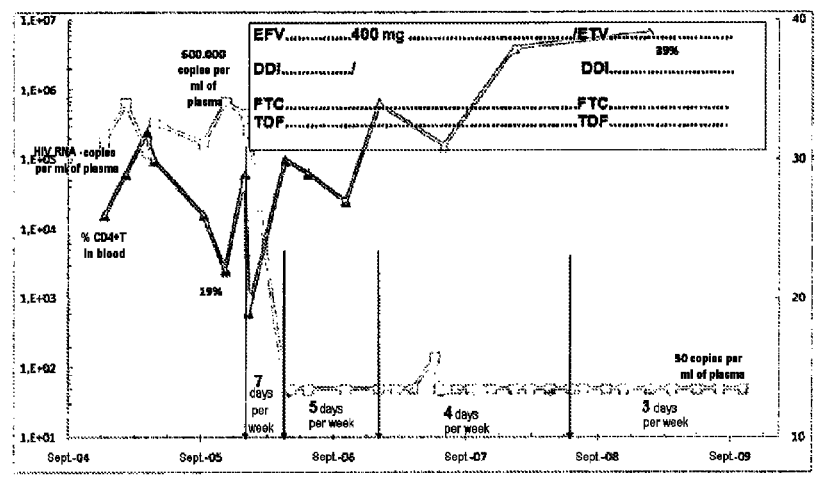
Fig.13 (Example 13)
FTC : emtricitabine ; DDI : didanosine ; TDF : tenofovir ; EFV : efavirenz ; ETV : etravirine.

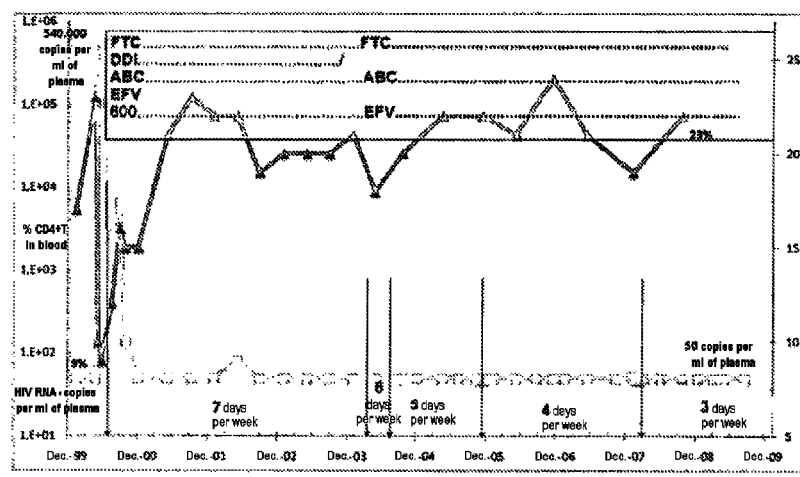
Fig.14 (Example 14)
TDF : tenofovir ; DDI : didanosine ; ABC : abacavir ; EFV : efavirenz.

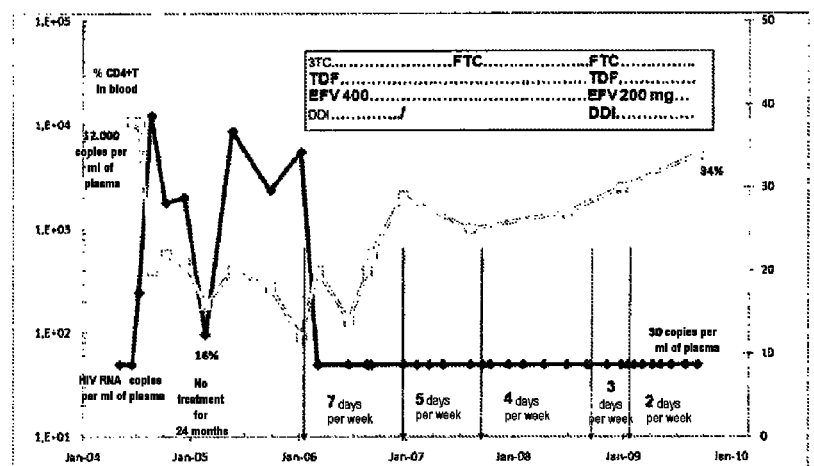
Fig.15 (Example15)
3TC : lamivudine ; FTC : emtricitabine ; DDI : didanosine ; TDF : tenofovir ; EFV : efavirenz.

2

SCHEDULES FOR ADMINISTERING COMBINATION THERAPIES USEFUL FOR TREATING PERSONS AFFLICTED WITH THE HUMAN IMMUNODEFICIENCY VIRUS (HIV)

CROSS REFERENCE TO RELATED APPLICATION

This is a National Stage of International Application No. PCT/EP2010/067851, filed 19 Nov. 2010, which claims the benefit of application Ser. No. 09/176,666.7, filed in Europe on 20 Nov. 2009, the disclosures of which Applications are incorporated by reference herein.

The present invention relates to novel schedules for administering combination therapies useful for treating persons afflicted with the human immunodeficiency virus (HIV), which is responsible for the acquired immune deficiency syndrome (AIDS).

The human immunodeficiency virus (or HIV) is a retrovirus of the genus *Lentivirus*, i.e. a virus with a long period of incubation, which implies slow development of the disease.

Like all viruses, HIV is incapable of multiplying on its own. It must first invade a cell and take control of it. The target cells of HIV are those presenting CD4 receptors on their surface. Thus, CD4+ lymphocytes, macrophages, dendritic cells and cerebral microglial cells can be infected with HIV.

When HIV infects a target cell, it takes control of it. Then the virus begins to make new copies of itself: this is the reproduction or replication phase. The virions thus produced infect other cells. In the absence of treatment, experts estimate that HIV can make up to 10 billion viral copies per day.

Two serotypes of HIV have been identified to date: HIV-1, which is present in most countries in the world, and HIV-2, which occurs mainly in West Africa.

It is commonly assumed that replication of the virus takes place in several main steps:

1—Fixation or attachment to a target cell
2—Fusion, penetration and decapsidation
3—Reverse transcription This step is specific to retroviruses: in fact, as the latter have RNA and not DNA for their genome, an operation of transcription, "converting" viral RNA to viral DNA, which alone can be integrated in the genome of the target cell, is necessary. This transcription is performed by the enzyme reverse transcriptase (RT).

4—Integration

The double-stranded DNA thus formed, closely associated with integrase and other viral and cellular protein components in a complex called preintegration complex, enters the cell nucleus. The DNA is then integrated randomly in the genome of the target cell, under the action of the enzyme integrase.

5—Formation of messenger RNA (mRNA)
6—Splicing of the mRNA thus obtained
7—Translation of the mRNA
8—Maturation
9—Assembly The structural proteins of the virus (matrix, capsid and nucleocapsid) are produced in the form of polyproteins. At the end of the maturation step, the various proteins are linked together and are transported to the membrane of the target cell, where they join the viral membrane glycoproteins. Viral RNAs join the viral proteins. The structural proteins assemble to form the capsid (protein envelope covering the DNA or RNA, the whole being denoted by nucleocapsid) and the matrix, which surrounds this assembly.

10—Budding

The capsid emerges from the infected cell.

11—Maturation of the viruses

A viral protease cleaves the bonds that join the various structural proteins (matrix, capsid and nucleocapsid). Following these cleavages, the virions (viral particles together with their outer protein envelope (capsid) and their RNA or DNA molecules inside) then become infectious and are ready to infect new cells.

Once seropositivity has been established, regular monitoring of the patient is put in place. Two main factors are usually monitored in order to track the development of the disease:

1—The Level of CD4+ T Lymphocytes

The level of CD4+ T lymphocytes is used for monitoring the progression of infection towards immune deficiency caused by HIV. The CD4+ T lymphocyte count corresponds to the number of T4 cells present in the blood. A normal level in humans is between 500 and 1500 CD4+T/mm$^3$ of blood. It has generally been assumed that:

up to 500 CD4+T/mm$^3$ of blood, the patient can live normally without requiring treatment;

starting from 350 CD4+T/mm$^3$ of blood, the offer of antiviral treatment is discussed, the expected result being control of the reproduction activity of HIV, and, additionally, an at least partial rise in CD4+T level;

below 200 CD4+T/mm$^3$ of blood, the patient is regarded as immunodepressed, running the risk of contracting diseases defining full-blown AIDS. Antiviral treatment with or without antibiotic prophylaxis is the only treatment capable of avoiding these complications.

2—Viral Load

The concentration of HIV viral particles in a volume of blood gives an objective estimate of the total number of virions freshly produced by the infected subject's body. Measurement is made according to standardized methods that vary little from one laboratory to another if it uses these validated methods. The result is given in log 10 of the copy number/ml. The error in quantification (copy number of the virus) is such that a variation less than or equal to 0.5 is said to be not significant.

The difference between two measurements of viral load taken with a time interval allows the rate of reproduction of HIV to be evaluated and therefore the development of the infection. It is generally assumed that there is a link between the viral load and the level of immune deficiency, manifested by the disappearance of CD4+ T lymphocytes.

At the date of the present invention, the viral load is the best indicator of the development of the virus in the patient. Based on current knowledge, it can also be suggested that a patient whose plasma viral load is below 50 copies/ml can be considered as a "non-transmitter of infection" by the mucosal route.

At the date of the present invention, there is no pharmaceutical composition for definitively eradicating HIV in a person who has contracted the virus, but certain compositions are able to suppress the HIV replication, said control being demonstrated by maintenance of a viral load constantly below 50 copies/ml of plasma. This control is able to stop progression of the disease to AIDS, and gives a life expectancy for the HIV carrier, correctly treated, near or equal to that of persons of the same age and of the same sex.

Since the beginning of the 1980s, numerous studies have led to the identification of a large number of antiretrovirals whose function is to interfere and block the various mechanisms required for replication of the HIV virus, by targeting more particularly one or other enzyme of HIV required for its replication or by affecting the physicochemical mechanisms governing entry of the virus into the target cell.

At the date of the present invention, antiretrovirals constitute the only medicinal products usefully employed against HIV. The first and principal objective of this therapy, notably in a patient who is naive of any treatment, is to keep the viral load below the detection threshold of 50 copies/ml of plasma for as long as possible, otherwise the antiviral therapy risks losing its efficacy over time, owing to the emergence of viruses that are resistant to the antiviral drugs administered (Hammer S M, Saag M S, Schechter M, et al., Treatment for adult HIV infection: 2006 recommendations of the International AIDS Society-USA panel. Top HIV Med (2006) 14:827-43)

The anti-HIV drugs are classified in four main classes of antiretrovirals, differing in their mode of action on the HIV virus and against its reproduction and/or its propagation in the carrier's body:

First there are the inhibitors of reverse transcriptase, which inhibit the conversion of viral RNA to proviral DNA, the first step in replication of the virus from the viral RNA. In this class, a distinction is made between:
  nucleoside or nucleotide inhibitors of reverse transcriptase (NIRT); and
  non-nucleoside inhibitors (NNIRT)

The NIRTs correspond to the first class of antiretrovirals that were marketed. As examples of NIRT compounds, we may mention zidovudine (AZT, Retrovir®) and stavudine (d4T, Zerit®) (two thymidine analogs), didanosine (ddI, Videx®), abacavir (ABC, Ziagen®) and tenofovir (TDF, Viread®) (three adenosine analogs), and lamivudine (3TC, Epivir®) and emtricitabine (FTC, Emtriva®) (two cytosine analogs).

The NNIRTs are powerful selective inhibitors of HIV reverse transcriptase. As examples of NNIRT compounds we may mention nevirapine (NVP, Viramune®), etravirine (ETV, Intelence®), and efavirenz (EFV, Sustiva®). They are only active against HIV-1.

Next there are the inhibitors of HIV protease (PI) which act by inhibiting the action of the enzyme that directs the exact cutting of the viral proteins that are precursors of structures required for formation of the infectious HIV material, and notably the HIV virions, which are able to propagate in the organism and infect new permissive cells. Under the action of the inhibitors of HIV protease, pseudovirions are obtained, which are unable to infect new cells. As examples of PI compounds, we may mention, in their historical order of marketing, saquinavir (SQV, Invirase®), ritonavir (RTV, Norvir®), indinavir (IDV, Crixivan®), amprenavir (APV, Agenerase®), nelfinavir (NFV, Viracept®), atazanavir (ATZ, Reyataz®), fosamprenavir (FPV, Telzir®), tipranavir (TPV, Aptivus®), and darunavir (DRV, Prezista®).

Each of these PIs has the pharmacokinetic property of being eliminated rapidly from the patient's body by the cytochrome P450 pathway; partial blocking of this route of elimination by a product such as ritonavir, a powerful inhibitor of the cytochrome P450 functions, greatly prolongs the pharmaceutical lifetime of the PI prescribed. Ritonavir given at low doses "boosts" the anti-HIV protease administered to the patient at the same time, by increasing the levels in the blood, and prolonging its useful half-life in the organism.

There are also integrase inhibitors, which block the action of an enzyme of HW whose elective function is to trim the ends of the HW proviral DNA so as to make this DNA suitable to serve as a template for the transcription of the proviral DNA to HIV RNA. The integrase inhibitors make this enzyme instantly incapable of its function of DNA trimming, thus preventing reproduction of the viral genome in its target cell. As examples of integrase inhibitor compounds, we may mention raltegravir and elvitegravir (GS 9137).

Finally there are the fusion-lysis inhibitors, which are involved before the start of the biochemical cycle of HIV replication, by blocking the infectious progress of HIV at the level of certain proteins present on the surface of the virions, or by interfering with the binding capacities of these surface proteins with co-receptors that are present themselves on the surface of target cells of HIV. As examples of fusion-lysis inhibitor compounds, we may mention enfuvirtide (Fuzeon®) and maraviroc (Celsentri®).

Administered alone, most of the antiretrovirals have been shown to be only partially effective, and are generally incapable of sufficiently blocking the reproduction of HIV to obtain an optimum reduction in viral load or prevent it increasing again.

To overcome this deficiency, many combination therapies, and in particular triple therapies, have been developed over the years.

Triple therapy consists of the co-administration of three antiretrovirals, in the form of three different medicinal products administered separately, or in the form of a unit dosage form containing the three active principles.

Thanks to these combination therapies, and in particular the triple therapies used since 1996, mortality due to AIDS has been reduced significantly.

Based on their demonstrated efficacy, and their acceptability, the preferred antiretroviral combinations for starting anti-HIV therapy in patients without prior treatment have as their basis combinations of two NIRTs combined either with a PI boosted with ritonavir, or an NNIRT (Gazzard B. British HIV Association (BHIVA) guidelines for treatment of HIV-infected adults with antiretroviral therapy (2006). HIV Med (2006) 7:487-503).

Exceptionally, a third reverse transcriptase inhibitor is added to the combination consisting of a pair of nucleosides and an NNIRT to form a quadruple therapy, but the latter, as well as triple therapies combining three NIRTs, have not generally been validated.

Among the triple therapies available at the date of the present invention, we may mention triple therapies combining:
  a pair of NIRTs selected from:
    lamivudine or emtricitabine, and zidovudine;
    lamivudine or emtricitabine, and stavudine (however, these last two pairs of nucleoside analogs are generally ignored by prescribers in the West because of their undesirable metabolic effects);
    lamivudine or emtricitabine and abacavir;
    lamivudine or emtricitabine and tenofovir; or
    lamivudine or emtricitabine and didanosine;
  with the combination of ritonavir with a PI selected from lopinavir, fosamprenavir, atazanavir and darunavir; or
    with an NNIRT selected from nevirapine, efavirenz and etravirine However, many triple therapies available at the date of the present invention are characterized by viral breakthroughs, i.e. a viral load in the patient above 100 copies/ml of plasma measured during two close consecutive dosages; the level of "viral breakthroughs" increasing with the years of uninterrupted administration. In these cases, the level of breakthroughs rises to 10% or more of patients treated after just 48 weeks of treatment, and can exceed 20% or even 30% after 3 or 4 years of uninterrupted treatments. These breakthroughs are a sign of suboptimal antiviral combinations, and put forward many situations in which there may be a selection of HIV viruses bearing mutations of at least partial resistance to the medicinal components of the combination (First-line antiretroviral therapy with efavirenz or lopinavir/ritonavir plus two nucleoside analogs: the SUSKA study, a nonrandomized comparison from the VACH cohort, Pere Domingo et al., *Journal of Antimicrobial Chemotherapy* (2008) 61, 1348-1358). This is the case in particular with most triple therapies combining only three reverse transcriptase inhibitor components and triple therapies combining two reverse transcriptase inhibitor components with nevirapine. (*Risk of Early Virological Failure of Once-Daily Tenofovir-Emtricitabine plus Twice-Daily Nevirapine in Antiretroviral Therapy—Naive HIV-Infected Patients*, Giuseppe Lapadula, Silvia Costarelli, Eugenia Quiros-Roldan, et al., *Clinical Infectious Diseases* 2008, 46:1127-1129; and *High rate of early virological failure with the once-daily tenofovir/lamivudine/nevirapine combination in naive HIV-1-infected patients—authors' response*, D. Rey, B. Hoen, P. Chavanet, et al., *J. Antimicrob. Chemother* 2009; 63: 1080-1081).

Furthermore, many undesirable side effects are associated with the use of these drugs, including lipodystrophies or abnormal distributions of solid fats in the body, linked mainly, if not exclusively, to antiviral combinations involving a nucleoside inhibitor from the family of thymidine analogs such as stavudine (d4T) or zidovudine (AZT); lactic acidosis characterized by deep, rapid breathing, somnolence, nausea, vomiting and/or stomach pains; sensations of vertigo; sleep disorders; difficulty concentrating; abnormal dreams; skin rashes; various inflammations or infections; and/or bone disorders, etc.

The number of triple therapies available at the date of the present invention means that each HIV patient can be administered different compositions during the treatment so that said treatment can be best adapted to the development of the infection and to the patient's tolerance. However, the need for daily administration seven days a week makes these therapies onerous and restricting for the patients, and tends to increase the intensity of the side effects that they experience.

At the date of the present invention, two triple therapies (Trizivir®, a medicinal product marketed by the GlaxoSmithKline pharmaceutical laboratory and Atripla®, a medicinal product marketed by the Gilead pharmaceutical laboratory) allow daily administration of the treatment seven days a week as a unit dosage form.

Trizivir® is in the form of a single film-coated tablet comprising:
  150 mg of lamivudine;
  300 mg of zidovudine; and
  300 mg of abacavir base (351 mg of abacavir sulfate).
    Atripla® is in the form of a single film-coated tablet comprising:
    600 mg of efavirenz;
    200 mg of emtricitabine; and
    245 mg of tenofovir disoproxil fumarate (expressed as tenofovir disoproxil).

This second pharmaceutical composition, which is among the most effective triple therapies currently marketed, nevertheless requires daily administration seven days a week, which certainly does not promote best patient compliance with the treatment.

Moreover, neither Atripla®, nor Trizivir® were able to reduce the undesirable effects mentioned above.

Finally, the cost per patient and per year of the combination therapies available at the date of the present invention is still excessively high. For example, Atripla® is sold in France in the form of a bottle containing 30 tablets (i.e. a month of treatment) at the price of 834.30 €, or an annual cost per patient of about 10,000 €. Now, although the current treatments can greatly limit the development of the HIV virus in patients, in no case are they able to eradicate it. The cost of treating persons with HIV can therefore reach very substantial sums, which are likely to increase considerably in future.

In 2007, an isolated study attempted to demonstrate that it was possible to reduce the weekly administration of various existing triple therapies to five days (*Pilot Study of a Novel Short-Cycle Antiretroviral Treatment Interruption Strategy: 48-Week Results of the Five-Days-On, Two-Days-Off (FOTO) Study*, Calvin J. Cohen, M D, Amy E. Colson, Alexander G. Sheble-Hall, et al., *HIV Clin Trials* 2007; 8(1):19-23). In this study, conducted on thirty patients whose HIV virus is controlled durably by various uninterrupted triple therapies, the weekly treatment regimen was reduced to five days per week (with two days off). At the 24th and 48th week of this treatment, the virus was still under control in 26 out of 29 patients (89.6%). However, even the authors admit that the benefits seen in the "FOTO" study are still very uncertain and these dosage regimens should not be used before these results are confirmed in a larger study. Moreover, this document gives no indication regarding the possibility of a possible further reduction in the number of weekly administrations of the existing triple therapies. In particular, it emphasizes that intermittent treatments should be reserved for triple therapies with a non-nucleoside antiretroviral agent, such as efavirenz or nevirapine, with a long natural life-time in the body, thus ruling out combinations comprising agents having a short plasma half-life, such as the antiproteases (PI).

However, these studies are still isolated and, at the date of the present invention, most specialists agree in considering that a decrease in the number of weekly administrations of existing triple therapies would not fail to increase the number of viral breakthroughs in the patients treated. Thus, a decrease in the number of weekly administrations of existing triple therapies is generally associated with certain therapeutic failure. As an example, Professor Delfraissy regards non-compliance with the treatment as the main cause of therapeutic failure ("*Therapeutic management of persons infected with HIV—Report* 2004—Under the supervision of Professor Jean-François Delfraissy, 2004, Éditions Flammarion, p. 48-49).

Moreover, a study published after the "FOTO" study (*Relationship between Adherence Level, Type of the Antiretroviral Regimen, and Plasma HIV Type 1 RNA Viral Load: A Prospective Cohort Study*, M. Martin, E. Del Cacho, C. Codina, et al., *AIDS Research and Human Retroviruses*, October 2008, 24(10): 1263-1268. doi:10.1089/aid.2008.0141) well summarizes the predominant prejudice according to which reducing the amount of antivirals in a patient must lead to a resumption of HIV replication, in inverse proportion to the pressure exerted daily by the triple therapy in question. Thus, compared with patients observing the prescribed treatment at more than 90%, this study notes a risk of viral breakthrough:
  9 times greater in patients only complying with the treatment at 80 to 89.9%, or, for triple therapy assuming daily administration seven days a week, for patients taking their treatment about six days out of seven;
  45.6 times greater in patients only complying with the treatment at 70 to 79.9%, or, for triple therapy assuming daily administration seven days a week, for patients taking their treatment about five to six days out of seven; and 77.3 times greater in patients only complying with the treatment at less than 70%, or, for triple therapy assuming daily administration seven days a week, for patients taking their treatment less than five days out of seven.

Moreover, another study also published after the "FOTO" study (*Not all missed doses are the same: sustained NNRTI treatment interruptions predict HIV rebound at low-to-moderate adherence levels*, Parienti J J, Das-Douglas M, Massari V, Guzman D, Deeks S G, Verdon R, Bangsberg D. R., PLoS One, Jul. 30, 2008; 3(7):e2783) teaches that any interruption of treatment of more than 2 days increases the risks of virological "rebound", i.e. the risks of a resumption of HIV replication.

However, it was discovered, completely unexpectedly, that certain combination therapies could be administered to the patient according to an administration regimen different from that recommended and used in the context of HIV treatment at the date of the present invention, permitting a marked decrease in the number of weekly administrations of the treatment, but without affecting or lowering the efficacy of the latter.

The present invention therefore relates to a pharmaceutical composition for treating the human immunodeficiency virus (HIV) in a human being, comprising three or four active principles selected as being:
- a nucleoside inhibitor of reverse transcriptase (NIRT) selected from lamivudine and emtricitabine;
- a nucleoside or nucleotide inhibitor of reverse transcriptase (NIRT) selected from didanosine, abacavir and tenofovir; and
- the combination of ritonavir with a protease inhibitor (PI) selected from lopinavir, fosamprenavir, atazanavir and darunavir; or a non-nucleoside inhibitor of reverse transcriptase (NNIRT) selected from efavirenz and etravirine; for daily administration one to four days a week to said human being.

The pharmaceutical composition according to the invention makes it possible to reduce the number of weekly administrations to the patient, while maintaining efficacy at least comparable to that of the triple therapy considered when it is administered once a day and seven days a week to said patient.

Moreover, in the context of the present invention, it can of course be envisaged to administer, to the HIV patient, just one of the compositions according to the invention throughout his or her treatment or, conversely, administer several of the compositions of the invention successively during said treatment, so that the treatment is best adapted to the development of the disease. As an example, an HIV patient can thus be treated initially with a triple therapy combining emtricitabine (FTC), tenofovir (TDF) and efavirenz (EFV), then with a triple therapy combining emtricitabine (FTC), tenofovir (TDF) and atazanavir (ATZ) "boosted" with ritonavir (r); then with a triple therapy combining emtricitabine (FTC), tenofovir (TDF) and lopinavir (LPV) "boosted" with ritonavir (r); then with a triple therapy combining emtricitabine (FTC), tenofovir (TDF) and darunavir (DRV) "boosted" with ritonavir (r).

In the context of the present invention:
- HIV denotes exclusively HIV-1;
- "pharmaceutically acceptable salt" of an active principle means any salt of addition of said active principle with a mineral or organic acid by the action of such an acid in an organic or aqueous solvent such as an alcohol, a ketone, an ether or a chlorinated solvent, and which is pharmaceutically acceptable;
- "pharmaceutically acceptable derivative" of an active principle means any "prodrug" or "metabolite" of said active principle, as well as a pharmaceutically acceptable salt thereof;
- "prodrug" of an active principle means any compound whose biotransformation in the body leads to said active principle;
- "metabolite" of an active principle means any intermediate resulting from the transformation of said active principle in the body during a metabolic process;
- "daily administration" means administration once a day or administration once every 24 hours;
- "continuous schedule" means continuous therapeutic treatment of a patient, comprising the successive administration of one or more therapeutic compositions (including combination therapies, whether or not according to the invention), identical or different, each with its own regimen of therapeutic administration (number of daily administrations and number of days of administration over a given period, a week for example) and this without limit and not sequenced or spaced out over time, i.e. without interruption of treatment;
- lamivudine (or 3TC) denotes (2R,5S)-(−)-4-amino-1-[2-(hydroxymethyl)-1,3-oxathiolan-5-yl]-1H-pyrimidin-2-one, as well as pharmaceutically acceptable salts or derivatives thereof;
- emtricitabine (or FTC) denotes L-2',3'-dideoxy-5-fluoro-3'-thiacytidine, as well as pharmaceutically acceptable salts or derivatives thereof;
- didanosine (or DDI) denotes L 2',3'-dideoxyinosine, as well as pharmaceutically acceptable salts or derivatives thereof;
- abacavir (or ABC) denotes [(1S,4R)-4-[2-amino-6-(cyclopropylamino)-9H-purin-9-yl]cyclopent-2-enyl]methanol, as well as pharmaceutically acceptable salts or derivatives thereof, including abacavir sulfate;
- tenofovir (or TDF) denotes L (R)-9-(2-phosphonylmethoxypropyl)adenine, as well as pharmaceutically acceptable salts or derivatives thereof, including tenofovir disoproxil or tenofovir disoproxil fumarate.
- efavirenz (or EFV) denotes (S)-6-chloro-4-(cyclopropylethynyl)-1,4-dihydro-4-(trifluoromethyl)-2H-3,1-benzoxazin-2-one, as well as pharmaceutically acceptable salts or derivatives thereof;
- etravirine (or ETV) denotes 4-({6-amino-5-bromo-2-[(4-cyanophenyl)amino]pyrimidin-4-yl}oxy)-3,5-dimethylbenzonitrile, as well as pharmaceutically acceptable salts or derivatives thereof;
- ritonavir denotes 1,3-thiazol-5-ylmethyl N-[2S,3S,5S)-3-hydroxy-5-[(2S)-3-methyl-2-{[methyl ({[2-(propan-2-yl)-1,3-thiazol-4-yl]methyl}) carbamoyl] amino}butanamido]-1,6-diphenylhexan-2-yl] carbamate, as well as pharmaceutically acceptable salts or derivatives thereof;
- lopinavir (or ABT-378) denotes (2S)—N-[2S,4S,5S)-5-[2-(2,6-dimethylphenoxy) acetamido]-4-hydroxy-1,6-diphenylhexan-2-yl]-3-methyl-2-(2-oxo-1,3-diazinan-1-yl)butanamide, as well as pharmaceutically acceptable salts or derivatives thereof;
- fosamprenavir (or TZV) denotes {[2R,3S)-1-[N-(2-methylpropyl)(4-aminobenzene)sulfonamido]-3-({[(3S)-oxolan-3-yloxy]carbonyl}amino)-4-phenylbutan-2-yl] oxy}phosphonic acid, as well as pharmaceutically acceptable salts or derivatives thereof, including fosamprenavir calcium;

atazanavir (or ATZ) denotes methyl N-[(1S)-1-{[(2S,3S)-3-hydroxy-4-[(2S)-2-[(methoxycarbonyl)amino]-3,3-dimethyl-N'-{[4-(pyridin-2-yl)phenyl]methyl}butanehydrazido]-1-phenylbutan-2-yl]carbamoyl}-2,2-dimethylpropyl]carbamate, as well as pharmaceutically acceptable salts or derivatives thereof, including atazanavir calcium; and darunavir denotes [(1R,5S,6R)-2,8-dioxabicyclo[3.3.0]oct-6-yl]N-[(2S,3R)-4-[(4-aminophenyl) sulfonyl-(2-methylpropyl)amino]-3-hydroxy-1-phenyl-butan-2-yl] carbamate, as well as pharmaceutically acceptable salts or derivatives thereof, including darunavir ethanolate.

Preferably, the present invention relates to a pharmaceutical composition as defined above, in which the following features are selected, alone or in combination:
the "first" NIRT is selected as being emtricitabine;
the "second" NIRT is selected as being tenofovir or didanosine, more preferably the second NIRT is selected as being tenofovir;
the PI is selected as being darunavir or atazanavir, more preferably the PI is selected as being darunavir; and/or
the NNIRT is selected as being efavirenz.

Quite preferably, the present invention relates to a pharmaceutical composition comprising, as active principles, emtricitabine, tenofovir and efavirenz.

As other examples of pharmaceutical compositions according to the present invention, we may notably mention the pharmaceutical compositions comprising:
emtricitabine, didanosine and the combination of ritonavir with lopinavir;
emtricitabine, didanosine and the combination of ritonavir with fosamprenavir;
emtricitabine, didanosine and the combination of ritonavir with atazanavir;
emtricitabine, didanosine and the combination of ritonavir with darunavir;
emtricitabine, didanosine and efavirenz;
emtricitabine, didanosine and etravirine;
lamivudine, didanosine and the combination of ritonavir with lopinavir;
lamivudine, didanosine and the combination of ritonavir with fosamprenavir;
lamivudine, didanosine and the combination of ritonavir with atazanavir;
lamivudine, didanosine and the combination of ritonavir with darunavir;
lamivudine, didanosine and efavirenz;
lamivudine, didanosine and etravirine;
emtricitabine, abacavir and the combination of ritonavir with lopinavir;
emtricitabine, abacavir and the combination of ritonavir with fosamprenavir;
emtricitabine, abacavir and the combination of ritonavir with atazanavir;
emtricitabine, abacavir and the combination of ritonavir with darunavir;
emtricitabine, abacavir and efavirenz;
emtricitabine, abacavir and etravirine;
lamivudine, abacavir and the combination of ritonavir with lopinavir;
lamivudine, abacavir and the combination of ritonavir with fosamprenavir;
lamivudine, abacavir and the combination of ritonavir with atazanavir;
lamivudine, abacavir and the combination of ritonavir with darunavir;
lamivudine, abacavir and efavirenz;
lamivudine, abacavir and etravirine;
emtricitabine, tenofovir and the combination of ritonavir with lopinavir;
emtricitabine, tenofovir and the combination of ritonavir with fosamprenavir;
emtricitabine, tenofovir and the combination of ritonavir with atazanavir;
emtricitabine, tenofovir and the combination of ritonavir with darunavir;
emtricitabine, tenofovir and etravirine;
lamivudine, tenofovir and the combination of ritonavir with lopinavir;
lamivudine, tenofovir and the combination of ritonavir with fosamprenavir;
lamivudine, tenofovir and the combination of ritonavir with atazanavir;
lamivudine, tenofovir and the combination of ritonavir with darunavir;
lamivudine, tenofovir and efavirenz; and
lamivudine, tenofovir and etravirine;

The pharmaceutical composition according to the present invention contains the active principles in a sufficient amount to ensure the desired therapeutic effect, i.e. treatment of HIV, maintaining, in the patient treated, a viral load below 50 copies/ml, preferably less than or equal to 20 copies/ml.

If necessary, the pharmaceutical composition according to the present invention also makes it possible to maintain or increase the proportion of CD4+ T lymphocytes at a level preferably above the levels of CD4+T/mm$^3$ of the patient prior to effective treatment.

Preferably, the amounts of antiretrovirals used for preparing the pharmaceutical composition according to the invention are as follows:
from 200 to 400 mg of lamivudine;
from 100 to 300 mg of emtricitabine;
from 150 to 350 mg of didanosine;
from 500 to 700 mg of abacavir;
145 to 345 mg of tenofovir;
from 100 to 200 mg of ritonavir;
from 400 to 800 mg of lopinavir;
from 600 to 1400 mg of fosamprenavir;
from 200 to 400 mg of atazanavir;
from 600 to 1200 mg of darunavir;
100 to 700 mg of efavirenz;
300 to 500 mg of etravirine.

More preferably, the amounts of antiretrovirals used for preparing the pharmaceutical composition according to the invention are identical to those conventionally administered daily seven days a week to the patient according to the triple therapies known at the date of the present invention, i.e.:
300 mg of lamivudine;
200 mg of emtricitabine;
250 mg of didanosine;
600 mg of abacavir;
245 mg of tenofovir;
100 mg of ritonavir;
600 mg of lopinavir;
1200 mg of fosamprenavir;
300 or 400 mg of atazanavir;
800 or 900 mg of darunavir;
200, 400 or 600 mg of efavirenz;
400 mg of etravirine.

The pharmaceutical composition according to the present invention can be formulated in any pharmaceutical form necessary for its administration. In particular, in the case of administration by the oral route, the compositions according to the present invention can be formulated in the form of coated or uncoated, effervescent, soluble, orodispersible, enteric or modified-release tablets; sugar-coated tablets; hard capsules; soft capsules; granules; granulate; pills; pastilles. In the case of systemic administration, the composition according to the invention can be formulated in the form of sterile lyophilized powder for injection. The pharmaceutical compositions according to the present invention can therefore comprise, in addition to the active principles, any pharmaceutically acceptable excipient known by a person skilled in the art and which is necessary for preparing the pharmaceutical composition in the desired form.

The pharmaceutical composition according to the invention can be administered to the patient daily, one day, two days, three days or four days a week, while maintaining efficacy at least comparable to that of the triple therapy considered when it is administered daily seven days a week to said patient. Preferably, the present invention relates to a pharmaceutical composition as defined above for daily administration two to four days a week, more preferably three or four days a week.

The pharmaceutical composition according to the invention can be administered at any time of day, before, during or after meals, without any effect on the efficacy of the treatment.

The pharmaceutical composition according to the invention can be administered according to a continuous schedule.

The pharmaceutical composition according to the invention can be administered to any HIV patient. However, it will be preferable to administer the composition according to the present invention to a patient who has a viral load less than or equal to 50 copies/ml of plasma since at least one measurement, regardless of what therapeutic means was used in order to reach said level of viral load.

The three or four active principles constituting the pharmaceutical composition according to the invention can be administered in the form of a unit pharmaceutical composition comprising three or four active principles, permitting administration of said composition to the patient in a single dose. Separate administration of one or more of the active principles constituting the pharmaceutical composition according to the invention can also be envisaged. Thus, the present invention also relates to a pharmaceutical product containing:

a nucleoside inhibitor of reverse transcriptase (NIRT) selected from lamivudine and emtricitabine;
  another nucleoside or nucleotide inhibitor of reverse transcriptase (NIRT) selected from didanosine, abacavir and tenofovir; and
  the combination of ritonavir with a protease inhibitor (PI) selected from lopinavir, fosamprenavir, atazanavir and darunavir; or a non-nucleoside inhibitor of reverse transcriptase (NNIRT) selected from efavirenz and etravirine;

as combination product for simultaneous, separate or spread over time daily administration one to four days a week, for treating HIV in human being.

The pharmaceutical product according to the invention can of course be administered according to one of the administration regimens defined above.

As an example, the pharmaceutical product according to the present invention can be in the form of:

a unit dosage form containing an NIRT as defined above, a unit dosage form containing the other NIRT as defined above, a unit dosage form containing ritonavir and a unit dosage form containing the PI as defined above; or
  a unit dosage form containing an NIRT as defined above, a unit dosage form containing the other NIRT as defined above and a unit dosage form that is a combination of ritonavir with a PI as defined above; or
  a unit dosage form containing an NIRT as defined above and a unit dosage form containing the other NIRT and the combination of ritonavir with a PI as defined above; or
  a unit dosage form containing the two NIRTs as defined above, a unit dosage form containing ritonavir and a unit dosage form containing the PI as defined above; or
  a unit dosage form containing the two NIRTs as defined above and a unit dosage form that is a combination of ritonavir with a PI as defined above; or
  a unit dosage form containing an NIRT as defined above, a unit dosage form containing the other NIRT as defined above, a unit dosage form containing the NNIRT as defined above;
  a unit dosage form containing an NIRT as defined above and a unit dosage form containing the other NIRT and NNIRT as defined above; or
  a unit dosage form containing the two NIRTs as defined above and a unit dosage form containing the NNIRT as defined above; or The present invention also relates to the use of a pharmaceutical composition as defined above for preparing a medicinal product intended for treating HIV in a human being, said composition being administered daily one to four days a week, preferably two to four days a week, more preferably three or four days a week to said human being, and administration can be carried out according to a continuous schedule, or otherwise.

The present invention also relates to a method of treatment of HIV in a human being infected with this virus by daily administration of a pharmaceutical composition as defined above, one to four days a week, preferably two to four days a week, more preferably three or four days a week, and administration can be carried out according to a continuous schedule, or otherwise.

The present invention is illustrated non-exhaustively by the following examples.

In the following examples (examples 1 to 15), the daily doses of active principle used for treating the patients correspond, unless stated otherwise, to the following doses:

300 mg of lamivudine;
  200 mg of emtricitabine;
  250 mg of didanosine;
  600 mg of abacavir;
  245 mg of tenofovir;
  100 mg of ritonavir;
  400 or 600 mg of lopinavir;
  1200 mg of fosamprenavir;
  300 or 400 mg of atazanavir;
  900 mg of darunavir;
  600 mg of efavirenz;
  400 mg of etravirine.

BRIEF DESCRIPTION OF THE DRAWINGS

FIG. 1 is a graph showing the plasma viral load and the CD4+ T level in the blood measured in a patient infected with HIV with the protocol of example 1.

FIG. 2 is a graph showing the plasma viral load and the CD4+ T level in the blood measured in a patient infected with HIV with the protocol of example 2.

FIG. 3 is a graph showing the plasma viral load and the CD4+ T level in the blood measured in a patient infected with HIV with the protocol of example 3.

FIG. 4 is a graph showing the plasma viral load and the CD4+ T level in the blood measured in a patient infected with HIV with the protocol of example 4.

FIG. 5 is a graph showing the plasma viral load and the CD4+ T level in the blood measured in a patient infected with HIV with the protocol of example 5.

FIG. 6 is a graph showing the plasma viral load and the CD4+ T level in the blood measured in a patient infected with HIV with the protocol of example 6.

FIG. 7 is a graph showing the plasma viral load and the CD4+ T level in the blood measured in a patient infected with HIV with the protocol of example 7.

FIG. 8 is a graph showing the plasma viral load and the CD4+ T level in the blood measured in a patient infected with HIV with the protocol of example 8.

FIG. 9 is a graph showing the plasma viral load and the CD4+ T level in the blood measured in a patient infected with HIV with the protocol of example 9.

FIG. 10 is a graph showing the plasma viral load and the CD4+ T level in the blood measured in a patient infected with HIV with the protocol of example 10.

FIG. 11 is a graph showing the plasma viral load and the CD4+ T level in the blood measured in a patient infected with HIV with the protocol of example 11.

FIG. 12 is a graph showing the plasma viral load and the CD4+ T level in the blood measured in a patient infected with HIV with the protocol of example 12.

FIG. 13 is a graph showing the plasma viral load and the CD4+ T level in the blood measured in a patient infected with HIV with the protocol of example 13.

FIG. 14 is a graph showing the plasma viral load and the CD4+ T level in the blood measured in a patient infected with HIV with the protocol of example 14.

FIG. 15 is a graph showing the plasma viral load and the CD4+ T level in the blood measured in a patient infected with HIV with the protocol of example 15.

EXAMPLE 1

An HIV patient was treated according to the following protocol:
  treatment with a quadruple therapy;
  then treatment with a triple therapy combining emtricitabine (FTC), tenofovir (TDF) and lopinavir (LPV) "boosted" with ritonavir (r), administered daily 4 days a week;
  and finally treatment with a triple therapy combining emtricitabine (FTC), tenofovir (TDF) and atazanavir (ATZ) "boosted" with ritonavir (r), administered daily 4 days a week, then 3 days a week, then 2 days a week.

The plasma viral load and the CD4+T level in the blood were measured during this treatment.

The results are presented in FIG. 1.

Throughout the treatment period, the patient's plasma viral load remained less than or equal to 50 copies/ml of plasma without any viral breakthrough being observed. Moreover, a rise in the CD4+T level in the blood was also observed.

EXAMPLE 2

An HIV patient was treated according to the following protocol:
  treatment with a quadruple therapy;
  then treatment with a triple therapy combining emtricitabine (FTC), tenofovir (TDF) and efavirenz (EFV) administered daily 5 days a week;
  and finally treatment with a triple therapy combining emtricitabine (FTC), tenofovir (TDF) and lopinavir (LPV) "boosted" with ritonavir (r) (400 mg for 65 kg), administered daily 4 days a week, then 3 days a week.

The plasma viral load and the CD4+T level in the blood were measured during this treatment.

The results are presented in FIG. 2.

Throughout the treatment period, the patient's plasma viral load remained less than or equal to 50 copies/ml of plasma without any viral breakthrough being observed. Moreover, a rise in the CD4+T level in the blood was also observed.

EXAMPLE 3

An HIV patient was treated according to the following protocol:
  treatment with several quadruple therapies;
  then treatment with a triple therapy combining emtricitabine (FTC), tenofovir (TDF) and efavirenz (EFV) administered daily 7 days a week, then 5 days a week, then 4 days a week, then 3 days a week, then 2 days a week.

The plasma viral load and the CD4+T level in the blood were measured during this treatment.

The results are presented in FIG. 3.

Throughout the treatment period, the patient's plasma viral load remained less than or equal to 50 copies/ml of plasma without any viral breakthrough being observed. Moreover, a rise in the CD4+T level in the blood was also observed.

EXAMPLE 4

An HIV patient was treated according to the following protocol:
  treatment with a quadruple therapy;
  then treatment with a triple therapy combining emtricitabine (FTC), tenofovir (TDF) and efavirenz (EFV) administered daily 5 days a week;
  and finally treatment with a triple therapy combining emtricitabine (FTC), tenofovir (TDF) and atazanavir (ATZ) "boosted" with ritonavir (r), administered 4 days a week, then 3 days a week.

The plasma viral load and the CD4+T level in the blood were measured during this treatment.

The results are presented in FIG. 4.

Throughout the treatment period, the patient's plasma viral load remained less than or equal to 50 copies/ml of plasma without any viral breakthrough being observed. Moreover, a rise in the CD4+T level in the blood was also observed.

EXAMPLE 5

An HIV patient was treated according to the following protocol:
  treatment with a quadruple therapy;
  then treatment with a triple therapy combining emtricitabine (FTC), tenofovir (TDF) and atazanavir (ATZ) "boosted" with ritonavir (r), administered daily 5 days a week, then 4 days a week;
  and finally treatment with a triple therapy combining emtricitabine (FTC), tenofovir (TDF) and lopinavir (LPV) "boosted" with ritonavir (r) 400 mg, administered daily 3 days a week.

The plasma viral load and the CD4+T level in the blood were measured during this treatment.

The results are presented in FIG. 5.

Throughout the treatment period, the patient's plasma viral load remained less than or equal to 50 copies/ml of plasma without any viral breakthrough being observed. Moreover, a rise in the CD4+T level in the blood was also observed.

EXAMPLE 6

An HIV patient untreated for 10 months was treated according to the following protocol:
treatment with a triple therapy combining emtricitabine (FTC), tenofovir (TDF) and efavirenz 400 mg administered daily 7 days a week;
then treatment with a triple therapy combining emtricitabine (FTC), tenofovir (TDF) and atazanavir (ATZ) "boosted" with ritonavir (r), administered daily 5 days a week;
then treatment with a triple therapy combining emtricitabine (FTC), tenofovir (TDF) and lopinavir (LPV) "boosted" with ritonavir (r), administered daily 4 days a week;
and finally treatment with a triple therapy combining emtricitabine (FTC), tenofovir (TDF) and darunavir (DRV) "boosted" with ritonavir (r) 400 mg, administered daily 4 days a week, then 3 days a week.

The plasma viral load and the CD4+T level in the blood were measured during this treatment.

The results are presented in FIG. 6.

Throughout the treatment period, the patient's plasma viral load remained less than or equal to 50 copies/ml of plasma without any viral breakthrough being observed. Moreover, a rise in the CD4+T level in the blood was also observed.

EXAMPLE 7

An HIV patient was treated according to the following protocol:
treatment with a quadruple therapy;
then treatment with a triple therapy combining emtricitabine (FTC), tenofovir (TDF) and efavirenz 400 mg, administered daily 5 days a week, then 4 days a week, then 3 days a week.

The plasma viral load and the CD4+T level in the blood were measured during this treatment.

The results are presented in FIG. 7.

Throughout the treatment period, the patient's plasma viral load remained less than or equal to 50 copies/ml of plasma without any viral breakthrough being observed. Moreover, a rise in the CD4+T level in the blood was also observed.

EXAMPLE 8

An HIV patient was treated according to the following protocol:
treatment with a quadruple therapy;
then treatment with a triple therapy combining emtricitabine (FTC), tenofovir (TDF) and efavirenz, administered daily 5 days a week, then 4 days a week, then 3 days a week.

The plasma viral load and the CD4+T level in the blood were measured during this treatment.

The results are presented in FIG. 8.

Throughout the treatment period, the patient's plasma viral load remained less than or equal to 50 copies/ml of plasma without any viral breakthrough being observed. Moreover, a rise in the CD4+T level in the blood was also observed.

EXAMPLE 9

An HIV patient was treated according to the following protocol:
treatment with a quadruple therapy;
then treatment with a triple therapy combining emtricitabine (FTC), tenofovir (TDF) and efavirenz 400 mg, administered daily 5 days a week, then 4 days a week.

The plasma viral load and the CD4+T level in the blood were measured during this treatment.

The results are presented in FIG. 9.

Throughout the treatment period, the patient's plasma viral load remained less than or equal to 50 copies/ml of plasma without any viral breakthrough being observed. Moreover, a rise in the CD4+T level in the blood was also observed.

EXAMPLE 10

An HIV patient untreated for 80 days was treated according to the following protocol:
treatment with a triple therapy combining emtricitabine (FTC), tenofovir (TDF) and atazanavir (ATZ) "boosted" with ritonavir (r) administered daily 7 days a week;
then treatment with a triple therapy combining emtricitabine (FTC), tenofovir (TDF) and lopinavir (LPV) "boosted" with ritonavir (r), administered daily 7 days a week;
and finally treatment with a triple therapy combining emtricitabine (FTC), tenofovir (TDF) and efavirenz 400 mg, administered daily 5 days a week, then 4 days a week, then 3 days a week.

The plasma viral load and the CD4+T level in the blood were measured during this treatment.

The results are presented in FIG. 10.

Throughout the treatment period, the patient's plasma viral load remained less than or equal to 50 copies/ml of plasma without any viral breakthrough being observed. Moreover, a rise in the CD4+T level in the blood was also observed.

EXAMPLE 11

An HIV patient was treated with a triple therapy combining emtricitabine (FTC), tenofovir (TDF) and efavirenz, administered daily 7 days a week, then 5 days a week, then 4 days a week, then 3 days a week.

The plasma viral load and the CD4+T level in the blood were measured during this treatment.

The results are presented in FIG. 11.

Throughout the treatment period, the patient's plasma viral load remained less than or equal to 50 copies/ml of plasma without any viral breakthrough being observed. Moreover, a rise in the CD4+T level in the blood was also observed.

EXAMPLE 12

An HIV patient was treated according to the following protocol:
treatment with a quadruple therapy;
then treatment with a triple therapy combining emtricitabine (FTC), tenofovir (TDF) and efavirenz 400 mg, administered daily 5 days a week, then 4 days a week, then 3 days a week.

The plasma viral load and the CD4+T level in the blood were measured during this treatment.

The results are presented in FIG. 12.

Throughout the treatment period, the patient's plasma viral load remained less than or equal to 50 copies/ml of plasma without any viral breakthrough being observed. Moreover, a rise in the CD4+T level in the blood was also observed.

EXAMPLE 13

An HIV patient was treated according to the following protocol:
treatment with a quadruple therapy;
then treatment with a triple therapy combining emtricitabine (FTC), tenofovir (TDF) and efavirenz 400 mg, administered daily 4 days a week.

The plasma viral load and the CD4+T level in the blood were measured during this treatment.

The results are presented in FIG. 13.

Throughout the treatment period, the patient's plasma viral load remained less than or equal to 50 copies/ml of plasma without any viral breakthrough being observed. Moreover, a rise in the CD4+T level in the blood was also observed.

EXAMPLE 14

An HIV patient was treated according to the following protocol:
treatment with a quadruple therapy;
then treatment with a triple therapy combining tenofovir (TDF), abacavir and efavirenz, administered daily 6 days a week, then 5 days a week, then 4 days a week, then 3 days a week.

The plasma viral load and the CD4+T level in the blood were measured during this treatment.

The results are presented in FIG. 14.

Throughout the treatment period, the patient's plasma viral load remained less than or equal to 50 copies/ml of plasma without any viral breakthrough being observed. Moreover, a rise in the CD4+T level in the blood was also observed.

EXAMPLE 15

An HIV patient was treated according to the following protocol:
treatment with a quadruple therapy;
then treatment with a triple therapy combining emtricitabine (FTC), tenofovir (TDF) and efavirenz 400 mg, administered daily 4 days a week.

The plasma viral load and the CD4+T level in the blood were measured during this treatment.

The results are presented in FIG. 15.

Throughout the treatment period, the patient's plasma viral load remained less than or equal to 50 copies/ml of plasma without any viral breakthrough being observed. Moreover, a rise in the CD4+T level in the blood was also observed.

The invention claimed is:

1. A method for treatment of HIV in a human being infected with this virus by administration once in a 24 hour period and the administration being repeated no more than four times during a week to said human being of a pharmaceutical composition for treating the human immunodeficiency virus (HIV) in a human being comprising three or four active principles selected from the group consisting of:
a nucleoside reverse transcriptase inhibitor (NRTI) selected from lamivudine and emtricitabine;
another nucleoside or nucleotide reverse transcriptase inhibitor (NRTI) selected from didanosine, abacavir and tenofovir; and
the combination of ritonavir with a protease inhibitor (PI) selected from lopinavir, fosamprenavir, atazanavir and darunavir; or a non-nucleoside reverse transcriptase inhibitor (NNRTI) which is etravirine.

2. The method as claimed in claim 1, wherein an NRTI is emtricitabine.

3. The method as claimed in claim 1, wherein an NRTI is tenofovir or didanosine.

4. The method as claimed in claim 1, wherein the pharmaceutical composition comprises the combination of ritonavir with a PI, said PI being darunavir or atazanavir.

5. The method as claimed in claim 1, wherein the pharmaceutical composition comprises:
300 mg of lamivudine or 200 mg of emtricitabine;
250 mg of didanosine, 600 mg of abacavir or 245 mg of tenofovir;
100 mg of ritonavir in combination with 600 mg of lopinavir, 1200 mg of fosamprenavir, 300 or 400 mg of atazanavir or 800 or 900 mg of darunavir; or 400 mg of etravirine.

6. The method as claimed in claim 1 wherein the pharmaceutical composition is administered two to four days during the week.

7. The method as claimed in claim 1 wherein the pharmaceutical composition is administered three or four days during the week.

8. A method of treatment of HIV in a human being infected with this virus by daily administration of a pharmaceutical product containing:
a nucleoside reverse transcriptase inhibitor (NRTI) selected from lamivudine and emtricitabine;
another nucleoside or nucleotide reverse transcriptase inhibitor (NRTI) selected from didanosine, abacavir and tenofovir; and
the combination of ritonavir with a protease inhibitor (PI) selected from lopinavir, fosamprenavir, atazanavir and darunavir; or a non-nucleoside reverse transcriptase inhibitor (NNRTI) which is etravirine;
as combination product for simultaneous, separate or spread over time administration once in a 24 hour period and the administration being repeated no more than four times during a week.

* * * * *